United States Patent [19]

Finlan

[11] Patent Number: 5,064,619
[45] Date of Patent: Nov. 12, 1991

[54] BIOLOGICAL SENSORS

[75] Inventor: Martin F. Finlan, Aylesbury, England

[73] Assignee: Amersham International PLC, Buckinghamshire, England

[21] Appl. No.: 350,034

[22] Filed: May 10, 1989

[30] Foreign Application Priority Data

May 10, 1988 [GB] United Kingdom ............... 8811053
May 10, 1988 [GB] United Kingdom ............... 8811054

[51] Int. Cl.$^5$ ............................................. G01N 21/00
[52] U.S. Cl. ................................. 422/82.05; 422/68.1; 422/82.09; 356/318; 356/445; 436/805; 435/808
[58] Field of Search ............... 422/82.05, 82.11, 82.09, 422/68.1; 356/318, 445; 436/805; 435/808

[56] References Cited

U.S. PATENT DOCUMENTS

| | | |
|---|---|---|
| 3,645,631 | 2/1972 | Gupta . |
| 4,297,032 | 10/1981 | Temple . |
| 4,844,613 | 7/1989 | Batchelder et al. ................ 356/445 |
| 4,857,273 | 8/1989 | Stewart ........................... 422/82.05 |
| 4,880,752 | 11/1989 | Keck et al. ....................... 422/82.05 |
| 4,889,427 | 12/1989 | Van Veen et al. ................. 356/445 |

FOREIGN PATENT DOCUMENTS 0305109 3/1989 European Pat. Off. .
2173895 10/1986 United Kingdom .

OTHER PUBLICATIONS

Patent Abstracts of Japan, vol. 12, No. 88, Mar. 23, 1988, p. 4 P 678, "Photochemical Analyzer".
"Instantaneous Observation of Angular Scan-Attenuated Total Reflection Spectra", K. Oda and M. Fukui, *Optics Communications,* vol. 59, No. 5/6, Oct. 1, 1986, pp. 361–365.
"A One-Dimensional Focusing Critical Angle Refractometer for Mass Transfer Studies", K. W. Beach et al., *Review of Scientific Instruments,* vol. 43, No. 6, Jun. 1972, pp. 925–928.
"Surface Plasmon Resonance for Gas Detection and Biosensing", Liedberg, Nylander and Lundstrom, *Sensors and Actuators,* vol. 4, 1983, pp. 299–304.

*Primary Examiner*—Robert J. Warden
*Assistant Examiner*—Theresa A. Trembley
*Attorney, Agent, or Firm*—Wenderoth, Lind & Ponack

[57] ABSTRACT

A surface plasmon resonance (SPR) detector includes a laser source for generating radiation which is reflected off a concave reflector to a point or line of incidence on the interface between a glass slide and a metal layer. A single pencil beam from the laser is scanned by a moving mirror across a small arc, covering those angles of incidence within which surface plasmon resonance occurs. A sensitive, for example antibody, layer overlies the metal layer to form a combined layer, and a sample to be tested is passed across the antibody layer. Any binding which occurs with the antibody layer results in the refractive index of the layer changing, and this change may be detected by monitoring the strength of the beam internally reflected at the point or line. A light detector enables the beam to be measured.

13 Claims, 4 Drawing Sheets

BIOLOGICAL SENSORS

BACKGROUND OF THE INVENTION

This invention relates to sensors for use in biological, biochemical and chemical testing and in particular to immunosensors used to monitor the interaction of antibodies with their corresponding antigens.

When antibodies are immobilized on a surface, the properties of the surface change when a solution containing a corresponding antigen is brought into contact with the surface to thus allow the antigen to bind with the antibody. In particular, the change in the optical properties of the surface can be monitored with suitable apparatus.

The phenomenon of surface plasmon resonance (SPR) can be used to detect minute changes in the refractive index of the surface as the reaction between the antigen and the antibody proceeds. Surface plasmon resonance is the oscillation of the plasma of free electrons which exists at a metal boundary. These oscillations are affected by the refractive index of the material adjacent the metal surface and it is this that forms the basis of the sensor mechanism. Surface plasmon resonance may be achieved by using the evanescent wave which is generated when a p-polarized light beam is totally internally reflected at the boundary of a medium, e.g. glass, which has a high dielectric constant. A paper describing the technique has been published under the title "Surface plasmon resonance for gas detection and biosensing" by Lieberg, Nylander and Lundstrom in Sensors and Actuators, Vol. 4, page 299. Illustrated in FIG. 1 of the accompanying drawings is a diagram of the equipment described in this paper. A beam 1 of light is applied from a laser source (not shown) onto an internal surface 2 of a glass body 3. A detector (not shown) monitors the internally reflected beam 4. Applied to the external surface 2 of glass body 3 is a thin film 5 of metal, for example gold or silver, and applied to the film 5 is a further thin film 6 of organic material containing antibodies. A sample 7 containing antigen is brought into contact with the antibody film 6 to thus cause a reaction between the antigen and the antibody. If binding occurs the refractive index of the film 6 will change owing to the increased size of the antibody molecules and this change can be detected and measured using the surface plasmon resonance techniques, as will now be explained.

Figure 1:
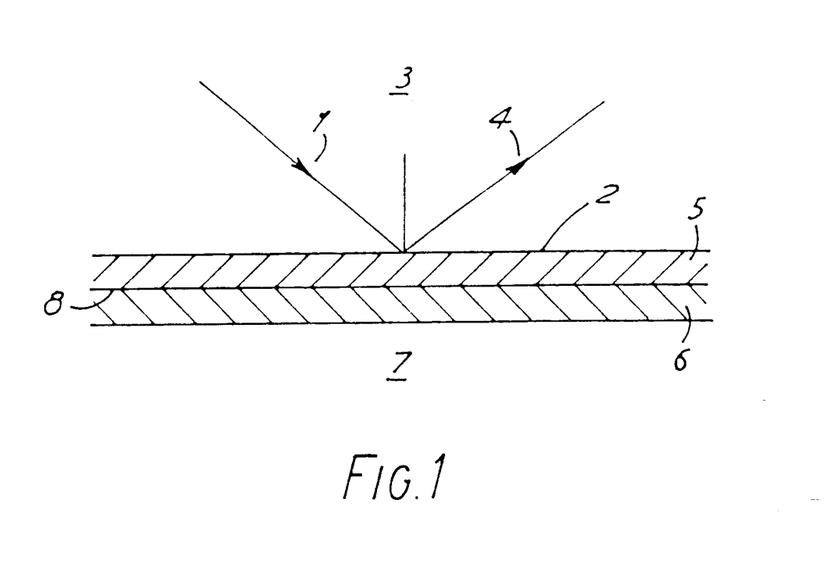
FIGS. 1 and 2 are diagrams of known experimental arrangements for demonstrating the surface plasmon resonance effect.

Surface plasmon resonance can be experimentally observed, in the arrangement of FIG. 1, by varying the angle of the incident beam 1 and monitoring the intensity of the internally reflected beam 4. At a certain angle of incidence the parallel component of the light momentum will match with the dispersion for surface plasmons at the opposite surface 8 of the metal film. Provided that the thickness of metal film 5 is chosen correctly there will be an electromagnetic coupling between the glass/metal interface at surface 2 and the metal/antibody interface at surface 8 which results in surface plasmon resonance and thus an attenuation in the reflected beam 4 at that particular angle of incidence. Thus, as the angle of incidence of beam 1 is varied, surface plasmon resonance is observed as a sharp dip in the intensity of the internally reflected beam 4 at a particular angle of incidence. The angle of incidence at which resonance occurs is affected by the refractive index of the material against the metal film 5—i.e. the antibody film 6—and the angle of incidence corresponding to resonance is thus a direct measure of the state of the reaction between the antibody and the antigen. Increased sensitivity can be obtained by choosing an angle of incidence half way down the reflectance dip curve, where the response is substantially linear, at the beginning of the antibody/antigen reaction, and then maintaining that angle of incidence fixed and observing changes in the intensity of the reflected beam 4 with time.

Known systems of the type described with reference to FIG. 1 utilize a prism as the glass body 3. A diagram showing this arrangement is given in FIG. 2 which is simply an experimental set up intended to demonstrate surface plasmon resonance. The prism is shown under reference 8 and has applied to its undersurface a thin film 5 of metal. Light 1 from a laser source (not shown) is incident on the prism where it is refracted at point 9 before entering the prism. The internally reflected beam 4 is likewise refracted (at point 10) upon exiting from the prism.

Figure 2:
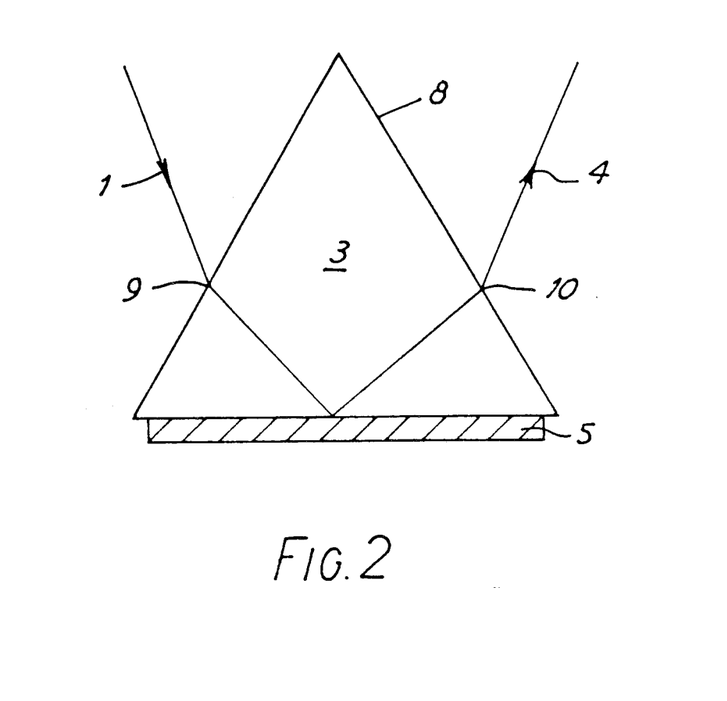

One problem with the prism is that, as the angle of incidence is changed, either by moving the source, or rotating the prism, or both, the point on surface 2 at which the incoming beam is incident moves. Because of inevitable variations in the metal film 5 and the antibody film 6, the angle of incidence which results in resonance changes as this movement occurs, which in turn introduces a further variable factor into the measurement and thus makes comparisons between the initial unbound, state and the bound state of the antibody film 6 less accurate.

SUMMARY OF THE INVENTION

An object of the present invention is the disadvantages of the known arrangements eliminate or reduce by replacing the essentially refractive optics such known arrangements by reflective optics. Reflective optics as used herein means that light from the light source is applied to the transparent block in which surface plasmon resonance is generated via at least one reflecting element such as a mirror.

In order to create the conditions necessary for surface resonance to occur, it is still necessary to provide a block of transparent material, usually glass, through which the light is passed in order to create a surface at which internal reflection takes place. However, as will be explained, this block could be any shape because the refraction which this block inevitably introduces can either be ignored (because it is insignificant), or can be compensated for in the reflective optics. As an example, the block may take the form of a thin glass plate, such as are used for microscope slides, onto one surface of which is applied the metal and the antibody film in the manner illustrated in FIG. 1. Incoming light is applied to the opposite surface and refracts through it at the interface. If the angle of incidence is correct, internal reflection will take place in such a way as to produce surface plasmon resonance at the metal/glass interface, as explained above, and the emergent bean leaves the glass plate from the same surface on which it originally entered, another refraction taking place at the point of exit. Provided that the glass plate is thin enough, these two refractions do not adversely affect the operation of the device. However, if the plate is not so thin, or if the block is some other shape—for example prismatic such as shown in FIG. 2—then refraction at the glass/air interface, particularly in connecting with the incoming beam, can cause problems of the type mentioned above.

Provided reflective optics are used, as proposed for the present invention, then refractions can be compensated for by tailoring the optics in such a way that, whatever the angle of incidence within the range of interest about the dip, the light will always be incident on the metal/glass interface at a particular point. It is believed that the optics may be tailored for any reasonable shape of glass including, as has been mentioned, flat plates, or prisms, and may by the same token be used in conjunction with the semicylindrical and hemispherical blocks used in the apparatus described in our corresponding European Patent Application 0305109, or in conjunction with the optical waveguides (e.g. fiber optics) described in our corresponding European Patent Application 89300544.7 dated the 20th of January 1989.

Although the radiation used to obtain surface plasmon resonance is described throughout this Specification as being light, in theory surface plasmon resonance effects should be obtainable using electromagnetic radiation of other frequencies. However in practice the radiation concerned is likely to be within or near the optical region, and the word light should be interpreted accordingly.

The reflecting element is preferably such as to bring the light to a focus at the point of incidence on the glass/metal interface. Thus with a "solid" input beam of reasonable width, the input beam effectively becomes several beams incident upon the glass/metal interface over a range of angles. The arrangement is such that the range of angles span the angle of dip corresponding to surface plasmon resonance. The corresponding internally reflected beam is likewise effectively several beams and may be monitored by a large area detector, or by an array of angularly spaced detectors positioned to collect the whole emergent beam. Thus the detectors can encode the information from the whole of the dip within milliseconds.

The use of a "solid" beam, such as described above, and as described in our copending European Applications 0305109 and 89300544.7, means that the light incident on the glass/metal interface effectively spans a range of angles and thus, if this is centered around that angle of incidence which is necessary to produce surface plasmon resonance, then the whole dip can be "seen" simultaneously by the detector.

One problem with this is that, in order to simultaneously look at the whole of the output beam from such apparatus, a detector having a large sensitive area must be provided. In addition, because the information in the beam is distributed on a spatial basis, it is necessary that the detector incorporates some form of x-y positional information, as well as a simple intensity measurement. Such detectors do exist, in the form of "large area" detectors and multi-detector arrays, but they are very expensive.

In a preferred embodiment of the present invention, we use just a single narrow beam, and means are provided for causing its angle of incidence at the glass/metal interface to scan across a range of angles of incidence such as is suitable for viewing the dip resulting from surface plasmon resonance. If the center angle of such movement is chosen, for example, to be the angle at which surface plasmon resonance takes place, then the whole dip can be rapidly scanned. To effect scanning, scanning means are used to scan the output of the radiation source backwards and forwards about a small arc before it is applied to the focussing means. Alternatively, the scanning means may be operable to cause a continuous 360° sweep of the output of the radiation source—somewhat in the manner of the rotating light from a lighthouse—and to mask off all but a small arc of this sweep, which small arc is then applied to the focussing means. The focussing means is operable to ensure that the scanning beam is incident on the glass/metal interface at substantially the same point whatever the instantaneous scanning angle might be.

The scanning means may, for example take the form of a planar mirror which is oscillated backwards and forwards at a frequency of, for example 50 HZ. Alternatively, the scanning means may be such as to cause continuous rotation of the mirror at, for example, 50 r.p.s., thus resulting in the 360° swept beam referred to above. The mirror may be moved by a suitable motor and mechanical interconnection. Suitable examples are synchronous motors, DC servo motors and the like. The circuitry associated with the motor outputs a strobe pulse so that the detector which looks at the output beam—i.e. the beam which has been internally reflected at the glass/metal interface—is able, at any one instance of time, to identify the particular angle of incidence at which the input light is incident at the glass/metal interface. It will be seen that the information in the input light about the SPR reflectance dip is not obtained on a spatial basis, but on a time basis by synchronizing the scanning of the input beam with the information output from the detector to build up a "picture" of the dip as the reaction between the antigen and the antibody proceeds.

Because only a relatively narrow beam is being used, only a detector having a small active area is needed, and these are very cheap. Since the output beam will move as the input beam is scanned, it is necessary, at the output side, to provide means for bringing the output beam into a path which will ensure that it is intercepted by the detector, whatever the angle it leaves the glass/metal interface. This may be readily achieved with suitable output optics. In an alternative embodiment the detector may take the form of a large area detector which is positioned to intercept the output beam whatever its angle of incidence. Since the detector would only have to provide an intensity reading, and not an indication of the beam x-y position, the detector can be implemented quite cheaply, for example, in the form of an amorphous silicon device.

The mirror used to scan the input beam can additionally be used to cause the beam to scan in other planes to enable multiple tests to be carried out simultaneously. The scanning to move the beam about the SPR dip, as described above, is essentially a single-plane effect, the beam being incident at the glass/metal interface at a single point which is stationary. But moving the point of incidence, multiple tests can be carried out, in effect, simultaneously because the movement of the beam is very fast compared with the progress of the test or tests.

In one embodiment, the mirror is caused to scan additionally in a plane at right angles to the plane of scanning to produce, in effect, a second scanning movement. Instead of producing a single stationary point of incidence, a line of incidence is produced, caused by the point of incidence moving along the line as the second scanning movement of the mirror takes place. By using a multiple mirror arrangement, further lines, parallel to the first, can be scanned thus giving, in effect, two dimensional raster scanning of an area. All that is now necessary is to divide up the metal and antibody layers across the line or area being scanned to enable separate tests to be carried out at each such divided area. Depending upon the particular sample feeding arrangements used, this enables the effective simultaneous testing of a number of different analyticities within a given specimen, or a number of separate specimens. The separate divided areas may each have the same antibody or may have different antibodies, and one or more may have no antibodies at all, to act as "reference" areas.

The scanning arrangements may be such as to cause continuous scanning of the point of incidence across the line or area to be tested, in which case the circuitry associated with the apparatus will be designed to ascertain, on a time basis, just where the point of incidence is at any one time (and therefore which area is being tested) and relate this to the output of the detector. As an alternative, the scanning may be such as to cause the point of incidence to "hover" over each area to be tested for a time sufficient to enable scanning across the dip to be effected at that point before passing on to the next.

The shaping of the reflecting element can additionally be carried out in order to compensate for other irregularities, in particular refraction, as the light enters the glass block, in order to ensure that the light is always incident on as near as possible a single spot on the glass/metal interface at which surface plasmon resonance occurs. It is possible to obtain reflective surfaces having very complex shapes using precision cutting machinery under computer control. For example, diamond machined aluminum can be used as the reflective surface. In practice, with the requirement for the beam to be focussed at the glass/metal interface, the reflective surface will be generally concave with a shape close to parabolic. The exact shape, however, in two dimensions will be determined also by the nature and shape of the glass block, this shape being derived by suitable computer programming.

If desired, a characteristic modulation may be impressed on the electromagnetic radiation so that synchronous detection may be used to ensure that signals at the detector relating to the desired reflected radiation are adequately distinguishable from those undersired output signals relating to extraneous radiation or other noise sources that can affect the detector. Such modulation is particularly desirable when using a single large-area detector. Although the layer applied to the metal film is described herein as antibody layer for use in immunoassays, it will be seen that any sensitive layer whose refractive index changes upon an event occurring can be used to thus provide a sensitive detector having a wide variety of applications in the fields of biology, biochemistry and chemistry. The material comprising the sensitive layer may be specific to a particular entity within the sample or may be nonspecific (i.e. may interact with several species of entity within the sample). Examples of specific materials include recognition molecules such as the aforementioned antibodies which will specifically bind an analyticity of interest within the sample, DNA/RNA probes which will bind with their complements in the sample liquid, or lectins, glycoproteins or enzyme substrates, all of which are capable of recognizing and binding with the other partner in a bimolecular recognition pair.

Examples of non-specific materials include hydrophobic materials, for example in the form of a monolayer of phospholipid-type molecules to capture amphipathic molecules, or hydrophilic materials which would capture polysaccharides. Indeed, it has been found that the surface of the metal film itself can form an effective non-specific binding material. Silver or gold surfaces will bind proteins or polynucleotides such as DNA or RNA without the need for any further coating and, in this case a separate sensitive layer is effectively dispensed with altogether, and the surface of the metal film used directly for the capture of entities within the sample to be tested.

The metal film material is commonly silver or gold, usually applied by evaporation. The film needs to be as uniform as possible in order to cater for minute movement in the point of incidence of the incoming beam. It is assumed that a structured metal film will give the best resonance and there are various ways in which the glass body can be pretreated to improve the performance of the metal film and in particular to control the natural tendency of such films to form discontinuous islands:

1. Immersion in molten nitrates and other molten salts. This has the effect of introducing ions into the surface in a manner which can be structured and which can act as foci for island formation.

2. Ion bombardment of cold or hot glass to introduce nucleating sites. The removal of the more mobile ions has been demonstrated to reduce the thickness at which the evaporated film becomes continuous.

3. Electroless plating or electroplating over lightly evaporated films (0 to 100 angstroms thick). Electroless plated films survive to a greater thickness than evaporated films and could form more stable nuclei for subsequent coating.

4. Evaporating on to electroless plated films. The electroless plated films have a stronger tendency to form an island structure and to form bigger islands with greater spacing than evaporating films. This could be of advantage in tuning light of a prescribed wavelength.

Coating performance can also be improved by:

1. Controlling the glass surface temperature during coating. Using a higher temperature substrate increases the islands' size and the spacing between them and conversely.

2. Evaporating in the presence of a magnetic or electrostatic field or electron emission device to control the ion content of the vapor stream. The state of charge of the substrate is known to affect the island structure.

3. Controlling the angle of incidence of the evaporated vapor stream relative to the glass surface. The mobility of the evaporated atoms and hence their ability to form bigger islands is greater when the momentum of the atoms relative to the glass surface is increased.

BRIEF DESCRIPTION OF THE DRAWINGS

In order that the invention may be better understood, several embodiments thereof will now be described by way of example only and with reference to the accompaying drawings in which.

DETAILED DESCRIPTION OF THE PREFERRED EMBODIMENTS

Figure 3:
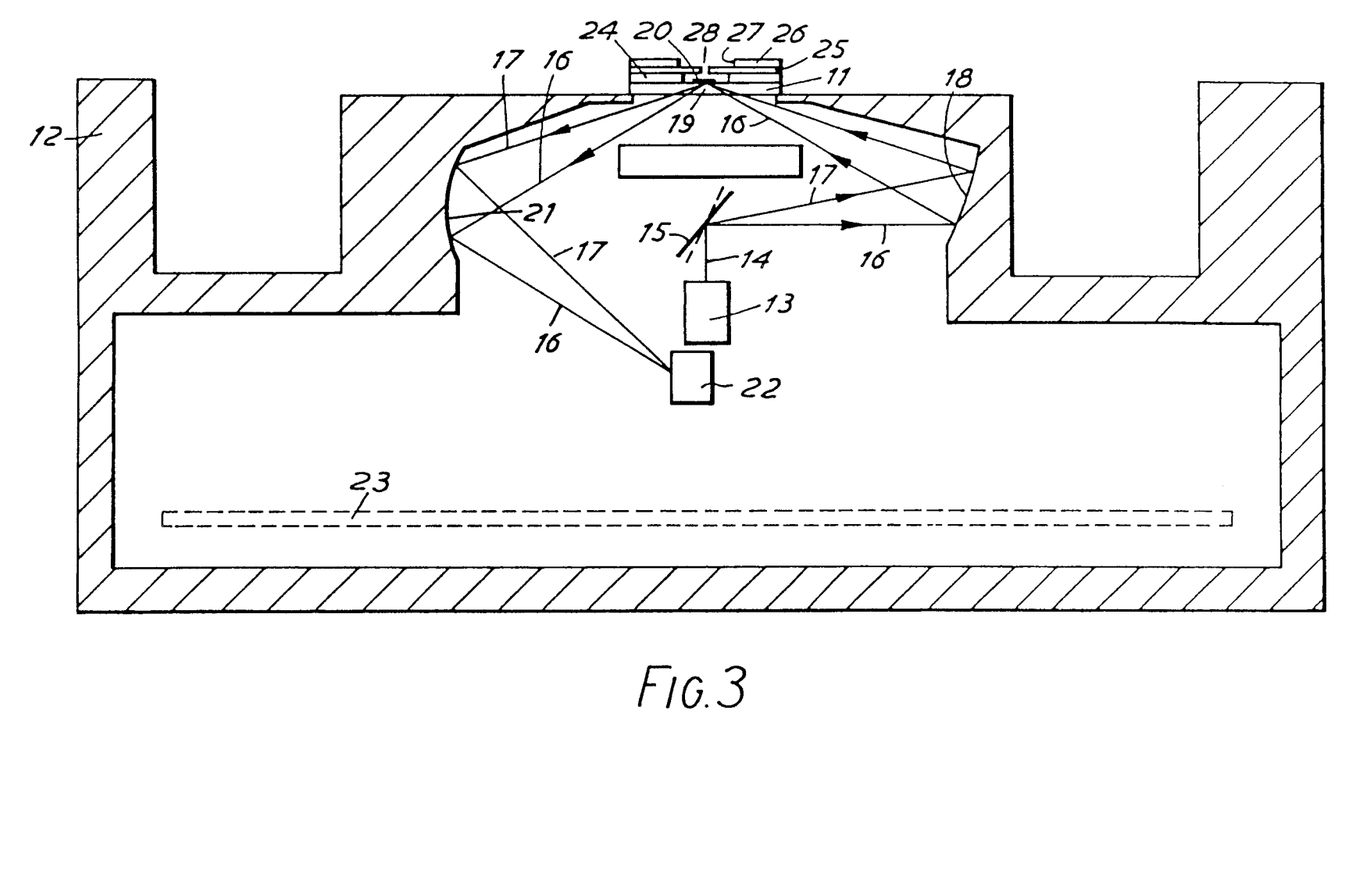
FIG. 3 is a diagrammatic side view of an embodiment of a sensor according to the present invention.

Referring to FIG. 3, the apparatus comprises a glass slide 11 of transparent material such as glass or quartz attached on a housing 12. A source 13 of electromagnetic radiation produces a collimated input beam 14 of electromagnetic radiation. The frequency of the radiation must be such as to result in the generation of surface plasmon waves and in practice will be within or near the visible region. Suitable sources include a helium neon laser or an infra red diode laser, but an ordinary light source, with suitable filters and collimators could be used.

A rotatable mirror 15 is used to scan the beam backwards and forwards between the limit positions shown by the beams 16, 17 whose ray patterns are traced through the apparatus. With the mirror in the position indicated by the solid line, the limit beam 16 results; with the mirror in the position indicated by the dotted line, the limit beam 17 results. The mirror is moved by a motor (not shown) energized in such a way as to cause the beam to continuously scan between the limit positions shown by the beams 16 and 17. The mirror 15 may be driven by a synchronous motor or DC servo motor or the like at a rotation speed typically of 50 HZ giving a scan period in the millisecond region. The beam from the mirror 15 is reflected off a generally concave reflecting surface 18 and is incident at a point 19 on the upper surface of the slide 11. This upper surface is formed with a metal film layer on top of which is an antibody or other sensitive layer, arranged in the manner illustrated in FIG. 1. The combined metal film/antibody layer is shown under reference 20. Radiation which is internally reflected at point 19 passes out of the slide and is reflected by a further generally concave reflecting surface 21 into a radiation sensitive detector 22 which gives an electrical output signal for analysis by associated circuitry mounted on a printed circuit board 23 within the housing.

The reflective surfaces 18, 21 are formed by machining of the material, for example aluminum, of the housing 12. If the housing is not fabricated from a suitable material, the reflective surfaces 18,21 can, of course, be formed as separate elements attached to the housing. Diamond machining of aluminum results in a highly reflective surface whose shape can be tailored, under computer control, to give whatever optical characteristics are required of it.

The layer 20 is restricted to a relatively small active zone about the point 19 and within a central hole provided in a circular disc 24 of absorbent material Overlying disc 24 are two further discs 25, 26 of non-absorbent material. A central aperture in upper disc 26 defines a well 27 into which a sample to be tested is placed. A central aperture in disc 25 is of a size to cause liquid in well 27 to travel through by capillary action into the active zone above layer 20. The thickness of disc 24 is such as to define a depth for the active zone such as to promote radially outwards movement of the sample liquid emerging from aperture 28 by capillary action. The absorbent disc 24 absorbs sample which has flowed past the active zone.

The whole unit comprising slide 11, disc 24 and discs 25 and 26 is disposable so that a fresh unit, including layer 20 can be used for each test.

In order to use the apparatus a sample to be tested, and containing an antigen capable of binding with the antibody molecules in layer 20, is placed in the well 27 and passes through aperture 28 by capillary action. Emerging from aperture 28, the liquid sample commences to flow rapidly outwards in all directions towards the absorbent disc 24, passing as it does so the layer 20. The sample adjacent the layer 20 is thus being constantly replenished during the course of the test, which ensures maximum sensitivity.

As the sample flows past the layer 20 any antigen within the sample capable of binding with the antibody in layer 20 will do so, thus altering the refractive index of layer 20 as the reaction proceeds. This change in refractive index is continuously monitored during the test by directing at the point 19 the light beam from source 13. Provided that conditions are correct—in particular the angle of incidence at the point 19 is correct—the application of the light beam will result in the generation of a plasmon wave, thus extracting energy from the input beam and causing an attenuation in the intensity of the output beam at a particular angle of incidence. The mirror 15 is oscillated backwards and forwards as the test proceeds so as to cause the beam to scan between the limit positions shown by beams 16, 17, as explained above. These limit positions are such as to cover the dip caused by the attenuation in the output beam. The circuitry controlling the mirror motor outputs a strobe signal to enable the detector 22 to identify the instantaneous angle at which the light is incident at the point 19, so that an accurate picture of the reflectance dip can be obtained.

The initial reflective dip which is chosen for setting up the limit beams 16, 17 may be taken from the dip which results when some neutral or buffer solution is passed through the cell, or when the sample under test is passed through the cell but before any reaction thereof has taken place. In connection with the latter method, it is to be noted that, as sample begins to flow past the active zone adjacent layer 20 the refractive index does not start to change immediately due to the antibody/antigen reaction. There is thus sufficient time to take an initial reading with the unreacted sample flowing past, which reading can be utilized, using feedback circuitry, to rapidly adjust the mirror 15 so that the center angle of incidence between that of the limit beams 16, 17 can be chosen correctly. This center angle may be chosen to be the actual angle of dip, or it may be an angle half way down the reflectance dip.

Although FIG. 3 shows the internal reflection needed to produce surface plasmon resonance being obtained from a thin glass slide 11, other geometrics are possible, and other methods of feeding the sample are also possible. Two alternative geometries are illustrated in FIGS. 4 and 5.

Figure 4:
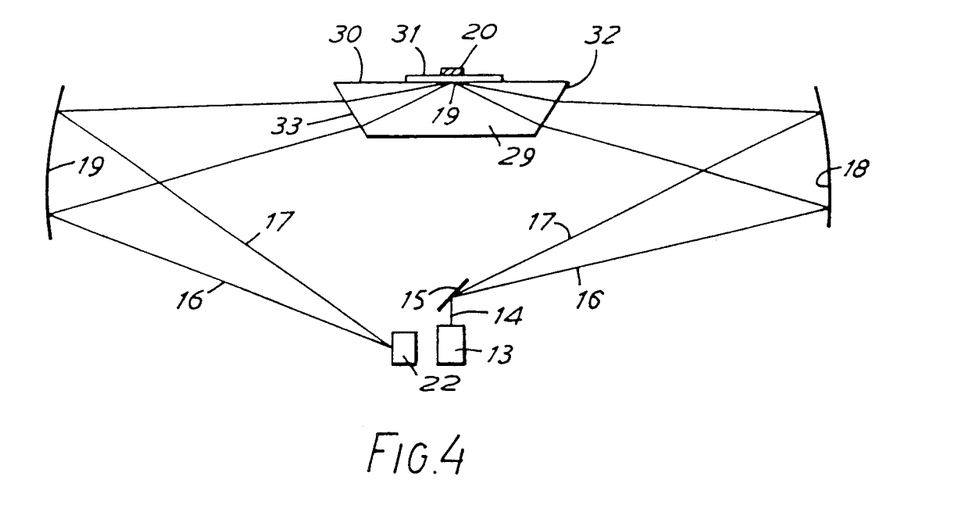
FIGS. 4 and 5 are ray diagrams showing the optical geometry of a prism and a rectangular slab.

In FIG. 4 the transparent block takes the form of a truncated prism 29, with the combined layer 20 applied to the base surface 30 of the prism. A glass slide 31 is optionally incorporated to provide a disposable assembly, as explained above. The slide, if used, is seated on the base surface 30 of the prism, using an optical coupling fluid. Light incident on the sloping input face 32 of the prism is subject to refraction and will result in the point 19 of incidence moving as the angle of the incoming beam is varied during scanning unless suitable measures are taken. As mentioned above, these measures may take the form of suitable tailoring of the shape of the reflective surface 18 to ensure that, whatever the angle of incidence, the light is always incident at the glass/metal interface at a single spot.

Similar comments apply to the refraction of the reflected beam at the output surface 33. In this case, it is desirable to bring the output beam to a point corresponding to the input of the detector 22, whatever the angle of incidence at the point 19. If this is not done a large area detector, or an array of detectors (both expensive), would be necessary to cover the inevitable large area which the moving beam would scan out by the time it reached the detector. Again, this can be achieved by suitable tailoring of the shape of reflective surface 19.

Figure 5:
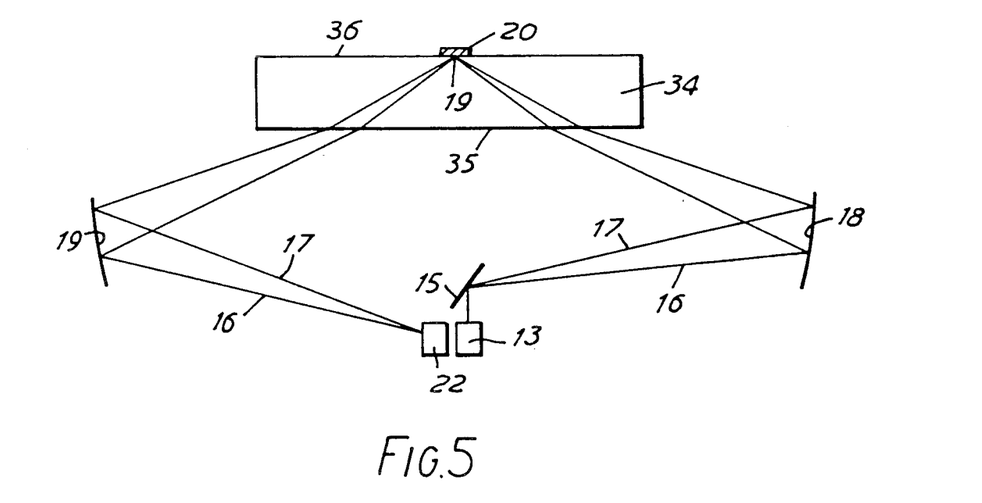

FIG. 5 shows an arrangement in which the transparent block takes the form of a rectangular block 34 in which the rays enter and leave the block through the surface 35 opposite to the surface 36 at which internal reflection takes place. As before a disposable slide can be used, but this is not shown in FIG. 5, the combined layer 20 being applied directly to the block.

Refraction takes place at the glass/air interface at surface 35 and this may be compensated for in the manner explained above by tailoring the shape of reflective surfaces 18 and 19. The arrangement of FIG. 5 is really no more than a version of the arrangement of FIG. 3, but in which the glass slide 11 of FIG. 3 is much thicker, thus exaggerating any errors due to refraction. In the case of a very thin glass slide, the errors associated with refraction may be small enough to be ignored but, if not, compensation can always be carried out, as explained above.

Figure 6:
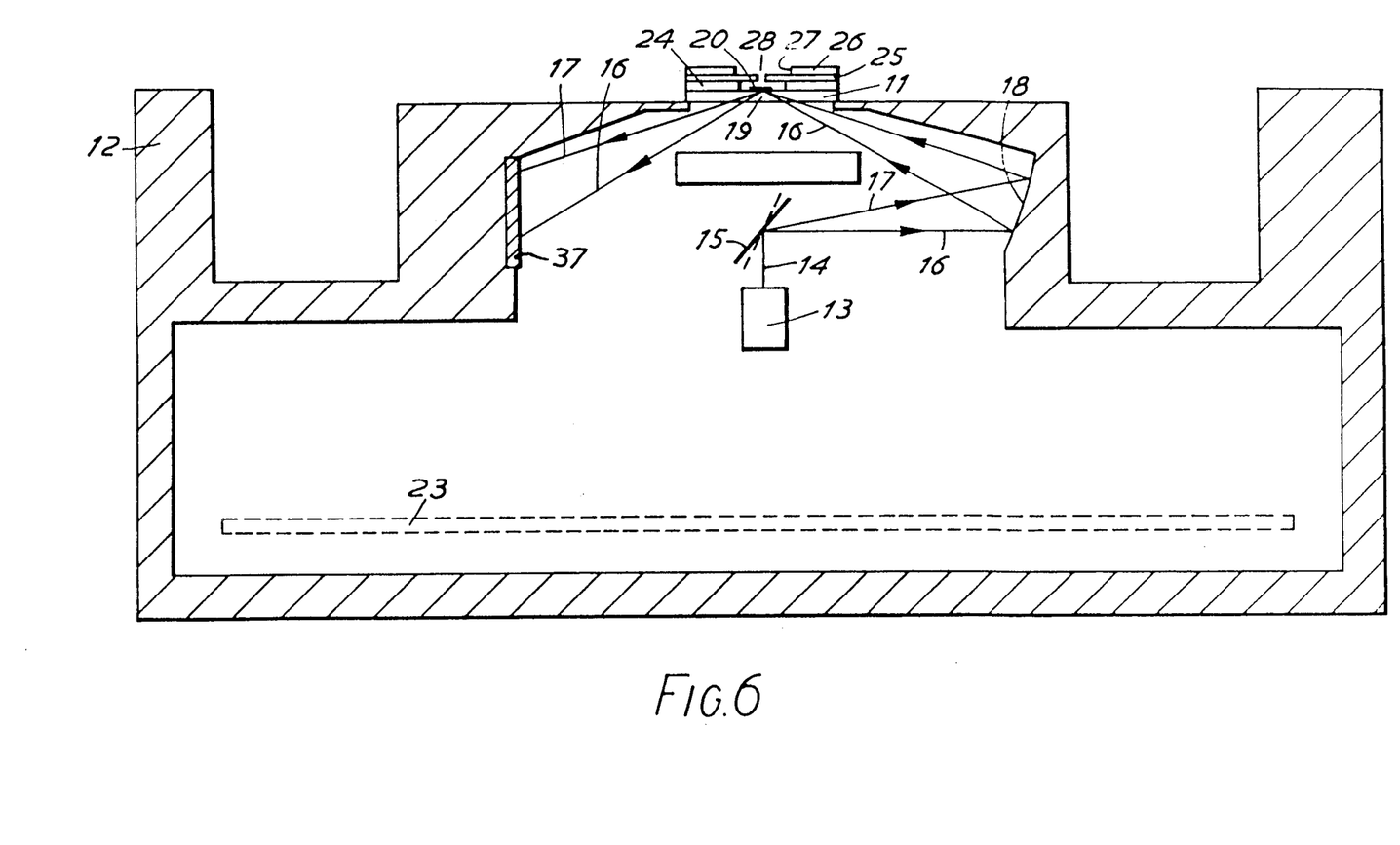
FIG. 6 is a view similar to FIG. 3, showing an alternative embodiment.

Reference is now made to FIG. 6 which shows an arrangement similar to that of FIG. 3, but in which the output reflecting surface 21 and the small light detector 22 are replaced by a large area light detector 37, such as an amorphous silicon device. The detector may be positioned in any convenient position and has a radiation sensitive area which is large enough to encompass the full movement of the output beam. Once again, the output from the detector is synchronized with the scanning of mirror 15 so that the circuitry is able to identify what the detector is looking at at any one instance of time. For this reason, it is not necessary to provide the detector 37 with any x-y positional detection since the information in the beam is on a time basis, rather than a positional basis.

The teaching of the present invention can also be applied to the apparatus described in our corresponding European Patent Applications 0305109 and 89300544.7, the disclosures of both of which are incorporated herein by this reference. In connection with the arrangement described in the latter application, the "input" reflective surface (reference 18) of the present invention would be used to bring the incoming beam to a focus at the input face of the optical waveguide (fiber optic).

Thus far it has been assumed that the mirror 15 will scan the beam 14 in substantially a single plane—that of the paper in FIGS. 3, 4, 5 and 6. Means may also be provided for scanning the beam backwards and forwards into and out of the plane of the paper, but at a slower rate, so that the point 19 moves along a line extending at right angles to the plane of FIGS. 3, 4 and 5. This enables a single beam to sequentially scan a plurality of separate active areas each having a distinct sensitive layer thereon. The beam can scan continuously over the active areas so formed, with appropriate synchronizing signals to tell the detector what it is looking at, or the mirror may scan (in this direction only) in a series of discrete steps so as to hover briefly over each active area for sufficient time to take a reading. In this way several analyticities within a single sample, or several separate samples, may be tested simultaneously for the same antibodies. Alternatively, each active area may have a different antibody, or some may be "reference" active areas.

In an alternative embodiment (not shown) a two dimensional array of active areas is provided on the top surface of the slide 11 and means are provided for causing the point 19 of incidence to raster (two dimensional) scan the active areas line by line. Thus, for example 80 active areas in a 10×8 array could be sampled in this way. Such scanning is readily carried out by a single mirror or more likely, a mirror system to give the two dimensional scanning. As before, scanning may be continuous, or the beam may halt momentarily over each active area for sufficient time for a reading to be taken.

It should be noted that scanning to obtain coverage of more than one active area is separate from the scanning used to alter the angle of incidence about the dip, although it may use the same mirror, moved in different planes. It should also be noted that scanning to cover multiple active areas may also be applied to the arrangements, such as those described in the aforementioned Patent Applications 8720854 and 8801807 in which a relatively wide input beam is focussed, by refractive or reflective optics, to the point 19 at which surface plasmon resonance occurs.

I claim:

1. A sensor for use in biological, biochemical or chemical testing, said sensor comprising: a block of material transparent to electromagnetic radiation; a layer of metallic material disposed over at least part of a first surface of said block; a layer of sensitive material disposed over the metallic material; means for introducing onto the sensitive layer so as to react therewith a sample to be analyzed; electromagnetic radiation producing means for producing a beam of electromagnetic radiation; reflective optic means for directing the beam into said transparent block in such a way as to be internally reflected off said at least part of the first surface of said block at an angle of incidence which will cause surface plasmon resonance to occur, said reflective optic means including a reflective element having a generally concave reflecting surface that from a given position will reflect beams of radiation impinging the reflecting surface at different locations thereon toward the same point on said at least one surface but at different respective angles of incidence; and detector means positioned in the sensor for receiving the internally reflected beam and for detecting the characteristics of the surface plasmon resonance that are dependent upon the reaction between the sample and the sensitive layer.

2. A sensor as claimed in claim 1, wherein the reflecting element is shaped to compensate for refractive effects as the beam enters the transparent block.

3. A sensor as claimed in either one of claims 1 or 2, wherein said electromagnetic radiation producing means produces a solid beam of radiation, the reflecting element reflecting the solid beam toward said first surface in such a way that the incoming beam is fan-shaped and spans a range of angles of incidence at said first surface which covers those which cause surface plasmon resonance to occur.

4. A sensor as claimed in either one of claims 1 or 2, further including scanning means, situated between said radiation producing means and said reflecting element, for continuously altering the angle of incidence of the beam that impinges the reflecting surface of said reflecting element, the reflecting element reflecting the beam at said first surface in such a way that the beam incident at said first surface has an angle of incidence which varies, with said scanning, about those angles which cause surface plasmon resonance to occur.

5. A sensor as claimed in claim 4, wherein said scanning means deflects the output beam from the radiation producing means backwards and forwards about a small arc.

6. A sensor as claimed in claim 4, wherein said scanning means comprises sweeping means for continuously sweeping the output beam from the radiation producing means over 360°, and means for masking off all but a small arc of the swept output beam for application to said transparent block.

7. A sensor as claimed in claim 4, wherein said sweeping means comprises a mirror onto which said radiation beam is incident, and means for rotating said mirror to in turn sweep the beam over 360°.

8. A sensor as claimed in claim 7, further including synchronizing means for synchronizing the mirror rotating means with information output from said detector means.

9. A sensor as claimed in claim 4, wherein said radiation source is a phased array source and said scanning means alters the phases of the individual sources making up said array in such a way that the output beam of radiation is caused to scan.

10. A sensor as claimed in claim 7, further including a second reflecting element positioned to receive radiation internally reflected at said first surface and directing such radiation into said detector means.

11. A sensor as claimed in claim 10, wherein said second reflecting element has a reflective surface so shaped as to reflect light toward the same point on said detector when the light impinges the reflecting element at any one of a plurality of locations thereon.

12. A sensor as claimed in either of claims 10 or 11, wherein said second reflecting element has a generally concave reflective surface.

13. A sensor as claimed in claim 7, wherein said detector means comprises a large area detector of a size sufficient to allow the internally reflected beam to be incident thereon whatever the emergent angle of said beam might be.

* * * * *